United States Patent [19]

Kawai et al.

[11] Patent Number: 4,885,162
[45] Date of Patent: Dec. 5, 1989

[54] POLYOLEFIN RESIN COMPOSITIONS

[75] Inventors: Yoichi Kawai; Takatoshi Udagawa; Takeshi Imakita, all of Kanagawa, Japan; Sachio Yokote, all of Kanagawa, Japan

[73] Assignee: Mitsui Toatsu Chemicals, Inc., Tokyo, Japan

[21] Appl. No.: 262,119

[22] Filed: Oct. 19, 1988

Related U.S. Application Data

[63] Continuation of Ser. No. 31,091, Mar. 26, 1987, abandoned.

[51] Int. Cl.$^4$ .............................................. A01N 31/14
[52] U.S. Cl. ........................................ 424/83; 514/721
[58] Field of Search ........................... 514/721; 424/83

[56] References Cited

U.S. PATENT DOCUMENTS 4,397,864 8/1983 Nakatani et al. ................ 514/461
4,599,362 7/1986 Nakatani et al. ................ 514/464

FOREIGN PATENT DOCUMENTS 544708 11/1985 Australia .
0142523 12/1978 Japan ................................... 424/83
0073009 6/1981 Japan ................................... 424/83
0152562 8/1985 Japan ................................... 424/83
151253 7/1986 Japan .
1152602 7/1986 Japan ................................. 514/721
2085006 4/1982 United Kingdom ............. 514/721

Primary Examiner—Leonard Schenkman
Attorney, Agent, or Firm—Kane, Dalsimer, Sullivan, Kurucz, Levy, Eisele and Richard

[57] ABSTRACT

Resin compositions comprising a polyolefin resin and an organic compound of the general formula (I):

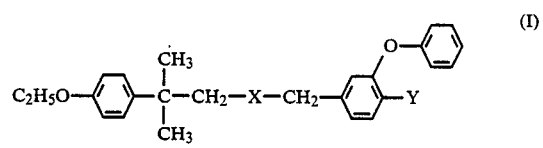

wherein
X represents an oxygen atom or —$CH_2$— and
Y represents a hydrogen or fluorine atom have insect-proofing effects, since said compound is kept on the surface of the composition to exhibit its insect-proofing effects.

7 Claims, No Drawings

POLYOLEFIN RESIN COMPOSITIONS

This is a continuation of co-pending application Ser. No. 031,091 filed on Mar. 26, 1987 now abandoned.

BACKGROUND OF THE INVENTION

1. Field of the Invention

The present invention relates to polyolefin resin compositions having excellent insect-proofing properties.

2. Related Art Statement

Polyolefin resins are used widely for the production of vessels for sundries, packing vessels and industrial parts in virtue of their excellent mechanical and chemical properties and hygienic safety.

The polyolefin resins are suitable particularly for the mass production because they can be molded easily. More particularly, they can be molded easily into a shape which could not be obtained or which was difficultly obtained from other ordinary materials. Thus, the uses of them are now being widened.

The utilization of the polyolefin resins for the production of household goods such as kitchen utensiles, e.g. cases and vessels built in household electric appliances, other cases and vessels, sinks, outer and inner plates of kitchen tables, floors, walls and ceilings is also increasing.

Further, the polyolefin resins are used for the production of cases for clothes and wardrobes.

The kitchen utensiles must be kept sanitary and the clothes in the cases must be kept from insects and moths.

For these purposes, insecticides and devices for capturing harmful insects are used.

However, they have defects that they are harmful to human bodies, that their smell soaks into the foods or clothes, that the devices are not nice to look at and that the devices are not effective for a long time and they must be renewed frequently.

Under these circumstances, the development of a highly useful material which is harmless to human bodies and which repels harmful insects has been expected to overcome the above-mentioned defects. However, no material having a high practical value which is moldable and which per se has the insect-proofing properties has been proposed yet.

Though an insect-proofing resin composition in the form of an emulsion or wax to be applied to a base in the form of a sheet such as a paper sheet has been proposed in the specification of Japanese Patent Laid-Open No. 115817/1978, this composition is utterly different from the polyolefin resin composition of the present invention, since the former cannot be molded and has no mechanical strength.

SUMMARY OF THE INVENTION

After intensive investigations made for the purpose of imparting excellent insecticidal effects to odorless polyolefin resins having a high hygienic safety, the inventors have found special insect-proofing organic compounds. The inventors have completed the present invention on the basis of this finding.

The present invention relates to a polyolefin resin composition characterized by comprising 100 parts by weight of a polyolefin resin and 0.0001 to 10 parts by weight of an organic compound of the general formula:

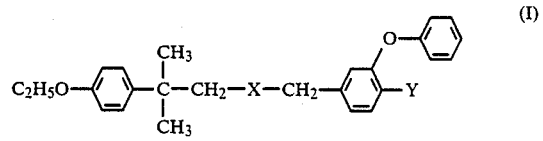

wherein
X represents an oxygen atom or $-CH_2-$ and
Y represents a hydrogen or fluorine atom.

The polyolefin resin composition of the present invention has an excellent effect of repelling or killing harmful insects over a long period of time.

DETAILED DESCRIPTION OF THE INVENTION

The polyolefin resins used in the present invention include, for example, high-density polyethylene, low-density polyethylene, medium-density polyethylene, polypropylene, ethylene/propylene copolymer, ethylene/butene-1 copolymer, polybutene-1 and poly(4-methylpentene-1). They can be used either alone or in the form of a mixture of them or a mixture thereof with another resin.

The insect-proofing organic compounds used in the present invention are those of the above general formula (I). These compounds can be produced easily by processes disclosed in the specifications of U.S. Pat. Nos. 4,397,864 and 4,599,362 and Australian Pat. No. 544,708.

When the polyolefin resin is used in combination with the compound of the above general formula (I), this compound is kept on the surface of the resin composition to exhibit the insect-proofing effects thereof over a long period of time and, thus, the excellent insect-proofing resin composition can be obtained. On the contrary, a resin composition comprising a combination of the compound of the general formula (I) with a styrene resin does not have the insect-proofing effect.

The compound of the above general formula (I) is used in an amount of 0.0001 to 10 parts by weight, preferably 0.001 to 2 parts by weight for 100 parts by weight of the polyolefin resin. When said amount is less than 0.0001 part by weight, the polyolefin resin composition scarcely has the insect-proofing property and, on the other hand, when it exceeds 10 parts by weight, the effect is no more increased remarkably and such a large amount is economically disadvantageous.

The resin composition of the present invention may contain, if necessary, other additives such as neutralizing agents, e.g. calcium stearate, magnesium hydroxide and aluminum hydroxide; antioxidants, e.g. 2,6-di-t-butyl-4-methylphenol, n-octadecyl-3-(3,5-di-t-butyl-4-hydroxyphenyl) propionate, pentaerythrityl-tetrakis[3-(3,5-di-t-butyl-4-hydroxyphenyl) propionate], tetrakis[2,4-di-t-butylphenyl) 4,4'-biphenylene diphosphonate, tris(2,4-di-t-butylphenyl) phosphite, dilaurylthio dipropionate and distearylthio dipropionate; U.V. absorbers, e.g. 2-(3-t-butyl-5-methyl-2-hydroxyphenyl)-5-methyl-2-hydroxyphenyl)-5-chlorobenzotriazole and bis(2,2,6,6-tetramethyl-4-piperidyl) sebacate; antistatic agents, e.g. glycerol monostearate, stearyl alcohol and bis(2-hydroxytaloamine); crystal nucleating agents, e.g. aluminum p-t-butylbenzoate, dibenzylidine-sorbitol and 1,3-2,4-di(ethylbenzylidene)sorbitol; pigments; dispersing agents, e.g. zinc stearate; peroxides; and inorganic fillers, e.g. talc, calcium carbonate, barium sulfate, glass fibers, mica and calcium silicate so far as the intended insect-proofing effect is not affected.

The resin composition of the present invention can be obtained by mixing the polyolefin resin, the organic compound of the above general formula (I) and, if necessary, other additives in a Henschel mixer or another blender to obtain a homogeneous dispersion and then melt-pelletizing this dispersion with an extruder.

The polyolefin resin composition of the present invention having excellent hygienic properties, odorlessness and insect-proofing effect can be molded by blow molding, sheet molding, vacuum molding, compression molding or another molding process to form food-storing cases, tableware-storing cases, cupboards and lockers, clothes boxes, chests of drawers, flowerpots, wall materials, floor materials, ceiling materials, etc. Namely, the above-mentioned cases, containers, devices, etc. produced from the polyolefin resin composition of the present invention repel the harmful insects and even when a harmful insect strays therein, it is killed. This effect lasts for a long period of time. The insect-proofing effect of the resin composition of the present invention is due to the organic compound of the above general formula (I). This effect lasts for a long period of time supposedly because said compound contained in the composition moves to the surface of the composition with time.

The following examples will further illustrate the present invention.

EXAMPLES 1 TO 3

0.1 part by weight (Example 1), 0.5 part by weight (Example 2) or 1.0 part by weight (Example 3) of 3-phenoxybenzyl 2-(4-ethoxyphenyl)-2-methylpropyl ether was added to a mixture of 100 parts by weight of polypropylene powder (trade name: Mitsui Noblen JHH; a product of Mitsui Toatsu Chemicals, Inc.), 0.05 part by weight of 2,6-di-t-butyl-p-cresol, 0.1 part by weight of pentaerythrityl-tetrakis[3-3,5-di-t-butyl-4-hydroxyphenyl) propionate], 0.1 part by weight of calcium stearate, 0.2 part by weight of glycerol monostearate, 0.1 part by weight of bis-(2-hydroxyltaloamine) and 0.1 part by weight of stearyl alcohol and the mixture was blended in a Henschel mixer. The mixture was extruded with an ordinary extruder at an extrusion temperature of about 220° C. to obtain pellets. The pellets were injection-molded into plates having a size of 160 mm×160 mm×2 mm with an injection-molding machine at a temperature of about 220° C.

The insect-proofing effects of the plates were examined.

In the test, the polypropylene plate was covered with a Petri dish having a diameter of 90 mm and a depth of 90 mm and 10 male German cockroaches were released therein. The number of knocked down cockroaches was counted at given time intervals.

The results are shown in Table 1.

EXAMPLES 4 TO 6

The same procedure as in Examples 1 to 3 was repeated except that 3-phenoxybenzyl 2-(4-ethoxyphenyl)-2-methylpropyl ether was replaced with 3-phenoxy-4-fluorobenzyl 2-(4-ethoxyphenyl)-2-methylpropyl ether in an amount of 0.1 part by weight (Example 4), 0.5 part by weight (Example 5) or 1.0 part by weight (Example 6) to obtain plates. The effects of the plates were examined in the same manner as above.

The results are shown in Table 1.

EXAMPLES 7 TO 9

The same procedure as in Examples 1 to 3 was repeated except that 3-phenoxybenzyl 2-(4-ethoxyphenyl)-2-methylpropyl ether was replaced with 1-(3-phenoxyphenyl)-4-(4-ethoxyphenyl)-4-methylpentane in an amount of 0.1 part by weight (Example 7), 0.5 part by weight (Example 8) or 1.0 part by weight (Example 9) to obtain plates. The effects of the plates were examined in the same manner as above.

The results are shown in Table 1.

EXAMPLES 10 TO 12

The same procedure as in Examples 1 to 3 was repeated except that 3-phenoxybenzyl 2-(4-ethoxyphenyl)-2-methylpropyl ether was replaced with 1-(3-phenoxy-4-fluorophenyl)-4-(4-ethoxyphenyl)-4-methylpentane in an amount of 0.1 part by weight (Example 10), 0.5 part by weight (Example 11) or 1.0 part by weight (Example 12) to obtain plates.

The effects of the plates were examined in the same manner as in Examples 1 to 3.

The results are shown in Table 1.

COMPARATIVE EXAMPLE 1

Plates were prepared in the same manner as in Example 1 except that 3-phenoxybenzyl 2-(4-ethoxyphenyl)-2-methylpropyl ether was not used.

The effects of the plates were examined in the same manner as above.

The results are shown in Table 1.

Tests of lasting properties:

The polypropylene plates containing the additives produced in Examples 2, 3, 4, 5, 6, 7, 8, 9, 10, 11 and 12 were left to stand in a constant temperature room at 25° C. for a long period of time (2, 4 and 6 months). After each period, male imagines of German cockroaches were brought into contact with the samples for 48 h and thereafter, the number of knocked down cockroaches was counted. The percentage of the knocked down cockroaches was calculated. For comparison, the same test as above was effected except that polypropylene plates free of said additive were used. The results are shown in Table 2.

The compounds used in the above examples, i.e. 3-phenoxybenzyl 2-(4-ethoxyphenyl)-2-methylpropyl ether, 3-phenoxy-4-fluorobenzyl 2-(4-ethoxyphenyl)-2-methylpropyl ether, 1-(3-phenoxyphenyl)-4-(4-ethoxyphenyl)-4-methylpentane and 1-(3-phenoxy-4-fluorophenyl)-4-(4-ethoxyphenyl)-4-methylpentane, were prepared by processes disclosed in the specifications of U.S. Pat. Nos. 4,397,864 and 4,599,362 and Australian Pat. No. 544,708.

TABLE 1

| | | Resin composition (parts by weight) | | Number of knocked down male German cockroaches *—1 (%) | | | | | | |
|---|---|---|---|---|---|---|---|---|---|---|
| | | Polypropylene | Insect-proofing agent *—2 | 4 h | 6 h | 24 h | 48 h | 72 h | 96 h | 120 h |
| Example | 1 | 100 | A 0.1 | 0 | 0 | 5 | 15 | 30 | 60 | 90 |
| | 2 | 100 | A 0.5 | 10 | 30 | 70 | 85 | 95 | 100 | 100 |
| | 3 | 100 | A 1.0 | 55 | 100 | 100 | 100 | 100 | 100 | 100 |
| | 4 | 100 | B 0.1 | 10 | 30 | 50 | 80 | 100 | 100 | 100 |
| | 5 | 100 | B 0.5 | 40 | 90 | 100 | 100 | 100 | 100 | 100 |
| | 6 | 100 | B 1.0 | 90 | 100 | 100 | 100 | 100 | 100 | 100 |
| | 7 | 100 | C 0.1 | 20 | 40 | 80 | 100 | 100 | 100 | 100 |
| | 8 | 100. | C 0.5 | 30 | 50 | 100 | 100 | 100 | 100 | 100 |
| | 9 | 100 | C 1.0 | 50 | 70 | 100 | 100 | 100 | 100 | 100 |
| | 10 | 100 | D 0.1 | 10 | 30 | 90 | 100 | 100 | 100 | 100 |
| | 11 | 100 | D 0.5 | 30 | 40 | 100 | 100 | 100 | 100 | 100 |
| | 12 | 100 | D 1.0 | 60 | 90 | 100 | 100 | 100 | 100 | 100 |
| Comparative Example | 1 | 100 | — | 0 | 0 | 0 | 0 | 0 | 0 | 0 |

*—1 The number of knocked down German cockroaches is the average of the percentages of five tests effected by using 10 cockroaches in each test.
*—2 A: 3-phenoxybenzyl 2-(4-ethoxyphenyl)-2-methylpropyl ether
B: 3-phenoxy-4-fluorobenzyl 2-(4-ethoxyphenyl)-2-methylpropyl ether
C: 1-(3-phenoxyphenyl)-4-(4-ethoxyphenyl)-4-methylpentane
D: 1-(3-phenoxy-4-fluorophenyl)-4-(4-ethoxyphenyl)-4-methylpentane

TABLE 2

| | | Resin composition (parts by weight) | | Number of knocked down male German Cockroaches* | | |
|---|---|---|---|---|---|---|
| | | Polypropylene | Additive | 2 months | 4 months | 6 months |
| Example | 2 | 100 | A-0.5 | 80 | 70 | 80 |
| | 3 | 100 | A-1.0 | 100 | 100 | 100 |
| | 4 | 100 | B-0.1 | 90 | 100 | 80 |
| | 5 | 100 | B-0.5 | 100 | 100 | 100 |
| | 6 | 100 | B-1.0 | 100 | 100 | 100 |
| | 7 | 100 | C-0.1 | 100 | 100 | 100 |
| | 8 | 100 | C-0.5 | 100 | 100 | 100 |
| | 9 | 100 | C-1.0 | 100 | 100 | 100 |
| | 10 | 100 | D-0.1 | 100 | 100 | 100 |
| | 11 | 100 | D-0.5 | 100 | 100 | 100 |
| | 12 | 100 | D-1.0 | 100 | 100 | 100 |
| Comparative Example | 1 | 100 | — | 0 | 0 | 0 |

The results were represented by the average of five tests.
It is apparent from the above-mentioned results that the polyolefin resin compositions of the present invention have excellent insect-proofing effects.

The results were represented by the average of five tests.

It is apparent from the above-mentioned results that the polyolefin resin compositions of the present invention have excellent insect-proofing effects.

What is claimed is:

1. A polyolefin resin composition which comprises; 100 parts by weight of a polyolefin resin and 0.0001 to 10 parts by weight of an organic compound of the formula:

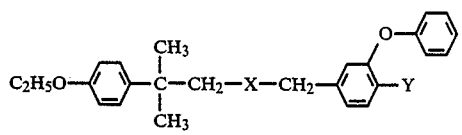

wherein
X represents an oxygen atom or —CH$_2$— and Y represents a hydrogen or fluorine atom;
said resin being selected from the group consisting of high-density polyethylene, low-density polyethylene, medium-density polyethylene, polypropylene, ethylene/propylene copolymer, ethylene/butene-1 copolymer, polybutene-1 and poly(4-methylpentene-1).

2. A composition according to claim 1 which contains 0.001 to 2 parts by weight of an organic compound of the general formula (I).

3. A composition according to claim 1 wherein the organic compound of the general formula (I) is 3-phenoxybenzyl 2-(4-ethoxyphenyl)-2-methylpropyl ether.

4. A composition according to claim 1 wherein the organic compound of the general formula (I) is 3-phenoxy-4-fluorobenzyl 2-(4-ethoxyphenyl)-2-methylpropyl ether.

5. A composition according to claim 1 wherein the organic compound of the general formula (I) is 1-(3-phenoxyphenyl)-4-(4-ethoxyphenyl)-4-methylpentane.

6. A composition according to claim 1 wherein the organic compound of the general formula (I) is 1-(3-phenoxy-4-fluorophenyl)-4-(4-ethoxyphenyl)-4-methylpentane.

7. A composition according to claim 1 wherein the polyolefin resin is polypropylene resin.

* * * * *